(12) United States Patent
Ichihara et al.

(10) Patent No.: US 9,592,316 B2
(45) Date of Patent: Mar. 14, 2017

(54) DISPOSABLE WEARING ARTICLE

(75) Inventors: Keiko Ichihara, Kagawa (JP); Toshiya Yago, Kagawa (JP); Naoto Ohashi, Kagawa (JP); Makoto Suekane, Kagawa (JP); Hiroki Ishikawa, Kagawa (JP)

(73) Assignee: Unicharm Corporation, Ehime (JP)

( * ) Notice: Subject to any disclaimer, the term of this patent is extended or adjusted under 35 U.S.C. 154(b) by 562 days.

(21) Appl. No.: 13/812,186

(22) PCT Filed: Jul. 19, 2011

(86) PCT No.: PCT/JP2011/066306
§ 371 (c)(1),
(2), (4) Date: Jan. 25, 2013

(87) PCT Pub. No.: WO2012/020623
PCT Pub. Date: Feb. 16, 2012

(65) Prior Publication Data
US 2013/0131619 A1 May 23, 2013

(30) Foreign Application Priority Data
Aug. 10, 2010 (JP) .................................. 2010-179818

(51) Int. Cl.
*A61F 13/42* (2006.01)
*A61L 15/56* (2006.01)
*A61F 13/531* (2006.01)

(52) U.S. Cl.
CPC .............. *A61L 15/56* (2013.01); *A61F 13/42* (2013.01); *A61F 2013/422* (2013.01); *A61F 2013/5312* (2013.01)

(58) Field of Classification Search
CPC ................ A61F 13/42; A61F 2013/422; A61F 13/53752; A61F 13/53756; A61F 2013/5315; A61F 2013/5317
(Continued)

(56) References Cited

U.S. PATENT DOCUMENTS 3,375,827 A * 4/1968 Bletzinger ........ A61F 13/53717
604/369
3,759,261 A * 9/1973 Wang ...................... A61F 13/42
116/200
(Continued)

FOREIGN PATENT DOCUMENTS

EP   1 685 816      8/2006
JP   2003-070837    3/2003
(Continued)

OTHER PUBLICATIONS

European Supplementary Search Report from corresponding European application No. 11816289.0 dated Mar. 14, 2014 (4 pgs).
(Continued)

*Primary Examiner* — Paula L Craig
(74) *Attorney, Agent, or Firm* — Brinks Gilson & Lione

(57) ABSTRACT

A disposable wearing article adapted to prevent indicators from being transferred to a liquid-absorbent structure and to make the indicators develop the color reaction quickly in response to a discharge of body exudates. A disposable diaper has a topsheet, a backsheet and a liquid-absorbent structure interposed between these top- and backsheets. A surface of a first backsheet facing the liquid-absorbent structure is formed with indicators. The indicators contain a hot-melt polymer, an indicator agent adapted to develop a color reaction and a plasticizing oil. The liquid-absorbent structure has a liquid-absorbent core, a liquid-diffusive wrapping sheet adapted to wrap the core. A hydrophilic bottom sheet is interposed between a bottom surface of the core and a bottom surface region of the wrapping sheet. A dimension in the transverse direction of the bottom sheet is larger than a dimension of a region in which the indicators are formed and smaller than a dimension in the transverse direction of the core.

6 Claims, 6 Drawing Sheets

(58) Field of Classification Search
USPC ..................................................... 604/361
See application file for complete search history.

(56) References Cited

U.S. PATENT DOCUMENTS

| | | | | |
|---|---|---|---|---|
| 4,229,813 | A * | 10/1980 | Lilly | G04F 13/06 116/206 |
| 4,681,576 | A * | 7/1987 | Colon | A61F 13/42 524/271 |
| 4,743,238 | A * | 5/1988 | Colon | A61F 13/42 523/111 |
| 4,931,051 | A * | 6/1990 | Castello | A61F 13/42 604/361 |
| 5,089,548 | A * | 2/1992 | Zimmel | A61F 13/42 523/111 |
| 5,300,054 | A * | 4/1994 | Feist | A61F 13/15203 604/358 |
| 5,354,289 | A * | 10/1994 | Mitchell | A61F 13/42 604/358 |
| 5,690,624 | A * | 11/1997 | Sasaki | A61F 13/42 604/361 |
| 5,762,641 | A * | 6/1998 | Bewick-Sonntag | A61F 13/15203 604/368 |
| 5,766,212 | A * | 6/1998 | Jitoe | A61F 13/42 604/361 |
| 5,895,379 | A * | 4/1999 | Litchholt | A61F 13/4755 604/368 |
| 6,258,996 | B1 * | 7/2001 | Goldman | A61L 15/60 604/358 |
| 6,297,424 | B1 * | 10/2001 | Olson | A61F 13/42 604/361 |
| 6,369,290 | B1 * | 4/2002 | Glaug | A61F 13/8405 424/490 |
| 6,372,952 | B1 * | 4/2002 | Lash | A61F 13/4755 604/369 |
| 6,495,734 | B1 * | 12/2002 | Fields | A61F 13/15203 604/378 |
| 6,649,809 | B2 * | 11/2003 | Fields | A61F 13/15203 604/374 |
| 6,653,522 | B1 * | 11/2003 | Blumenthal | A61F 13/42 524/275 |
| 6,673,982 | B1 * | 1/2004 | Chen | A61F 13/4751 604/378 |
| 6,747,185 | B2 * | 6/2004 | Inoue | A61F 13/42 604/361 |
| 7,102,054 | B1 * | 9/2006 | Cree et al. | 604/378 |
| 9,180,058 | B2 * | 11/2015 | Ichihara | A61F 13/42 |
| 2002/0165509 | A1 * | 11/2002 | Baer | A61F 13/15617 604/368 |
| 2003/0045845 | A1 | 3/2003 | Yoshioka | |
| 2004/0167489 | A1 * | 8/2004 | Kellenberger et al. | 604/385.01 |
| 2004/0191118 | A1 * | 9/2004 | Mody | G01N 31/222 422/401 |
| 2005/0113774 | A1 * | 5/2005 | Ishikawa | A61F 13/49019 604/378 |
| 2007/0100305 | A1 | 5/2007 | Isogai et al. | |
| 2009/0062757 | A1 * | 3/2009 | Long | A61F 13/42 604/361 |
| 2009/0326494 | A1 * | 12/2009 | Uchida et al. | 604/361 |
| 2010/0249737 | A1 * | 9/2010 | Ito | A61F 13/15634 604/367 |
| 2012/0089108 | A1 * | 4/2012 | Ueda | A61F 13/539 604/372 |

FOREIGN PATENT DOCUMENTS

| | | |
|---|---|---|
| JP | 2004-337386 | 12/2004 |
| JP | 2005-052190 | 3/2005 |
| JP | 2005-304826 | 11/2005 |
| JP | 2007-117649 | 5/2007 |
| JP | 2007-252659 | 10/2007 |
| JP | 2008-113686 | 5/2008 |

OTHER PUBLICATIONS

International Search Report based on corresponding PCT application No. PCT/JP2011/066306 dated Sep. 20, 2011 (4 pgs).

* cited by examiner

DISPOSABLE WEARING ARTICLE

RELATED APPLICATION

This application is a 35 U.S.C. §371 national phase filing of International Patent Application No. PCT/JP2011/066306, filed Jul. 19, 2011, through which and to which priority is claimed under 35 U.S.C. §119 to Japanese Patent Application No. 2010-179818, filed Aug. 10, 2010.

TECHNICAL FIELD

The present invention relates to disposable wearing articles and more particularly to disposable wearing articles such as disposable diapers, disposable toilet-training pants, disposable incontinent pants and disposable sanitary pants each provided in a crotch region thereof with indicators adapted to develop a color reaction in response to contact with moisture or body exudates.

BACKGROUND

Conventionally, disposable diapers each including front and rear waist regions and a crotch region extending between these front and rear waist regions wherein the crotch region is provided with an indicator adapted to detect the occurrence of urination are widely known. For example, JP 2007-252659 A (PTL 1) and JP 2004-337386 A (PTL 2) disclose disposable diapers each including top- and backsheets and an absorbent body interposed between these sheets. The backsheet is coated on the inner surface with the hot-melt composition containing the color reaction agent as the indicator. The liquid-permeable sheet is placed between the backsheet and the liquid-absorbent body so that these sheets may prevent the color reaction agent contained in the hot-melt composition from being transferred to the absorbent core.

If the color reaction agent is transferred to the absorbent core, there is a likelihood that the color reaction agent might develop a color reaction due to a slight amount of water vapor absorbed by the absorbent core from the atmosphere but by preventing such transfer of the color reaction agent to the core, the development of the color reaction of the indicators before actual use of the diaper can be prevented.

CITATION LIST

Patent Literature

{PTL 1}: JP 2007-252659 A
{PTL 2}: JP 2004-337386 A

SUMMARY

Technical Problem

According to the disclosure in PTL 1 and PTL 2, a dimension in the transverse direction of the liquid-permeable sheet located between the absorbent body and the backsheet is the same as that of the absorbent body. As a result, urine discharged onto the topsheet permeates the absorbent body and the liquid-permeable sheet and reaches the indicators. Urine comes in contact with the indicators by the intermediary of the liquid-permeable sheet and a correspondingly longer time is required for the indicators to develop a color reaction.

An object of the present invention is to provide a disposable wearing article adapted to prevent the indicator from being transferred to the liquid-absorbent structure and to cause the indicator to develop the color reaction quickly in response to a discharge of body exudates.

Solution to Problem

There is provided a disposable wearing article having a longitudinal direction and a transverse direction, and including a skin-facing side, a non-skin-facing side opposite to the skin-facing side, front and rear waist regions, a crotch region extending between the front and rear waist regions, a liquid-permeable topsheet lying on the skin-facing side, a liquid-impermeable backsheet lying on the non-skin-facing side and a liquid-absorbent structure interposed between these top- and backsheets and placed at least in the crotch region. The backsheet is formed on the surface thereof facing the liquid-absorbent structure with at least one indicator adapted to develop a color reaction when the at least one indicator comes in contact with at least one of moisture and body exudates.

The disposable wearing article according to the present invention further includes the following features:

the liquid-absorbent structure includes a liquid-absorbent core and a liquid-diffusive wrapping sheet adapted to wrap the skin-facing surface and the non-skin-facing surface of the core and being continuous outboard of the core in the transverse direction; and a bottom sheet formed of a hydrophilic fibrous nonwoven fabric is provided between the non-skin-facing surface of the core and the wrapping sheet so that the bottom sheet positionally corresponds to the at least one indicator wherein a dimension in the transverse direction of the bottom sheet is smaller than that of the core, and the at least one indicator contains a hot-melt polymer, an indicator agent adapted to develop a color reaction and a plasticizing oil, and the at least one indicator is adapted to put in direct contact with the wrapping sheet, wherein an oil absorbency of the wrapping sheet is higher than that of the bottom sheet.

According to one embodiment of the present invention, a Klemm's water absorbency of the wrapping sheet is higher than that of the bottom sheet.

According to another embodiment of the present invention, most of fibers of the bottom sheet has a fiber orientation along one of the longitudinal direction and the transverse direction and a region formed with the at least one indicator extends along the fiber orientation of the bottom sheet.

According to even another embodiment of the present invention, most of fibers of the wrapping sheet have a fiber orientation extending in one of the longitudinal direction and the transverse direction, and the wrapping sheet and the bottom sheet are layered on each other so that the fiber orientations of these two sheets coincide with each other.

According to still another embodiment of the present invention, the core contains at least superabsorbent polymer particles and a content percentage of the superabsorbent polymer particles is in a range of 35 to 70% by mass of a total mass of the core.

According to yet another embodiment of the present invention, a center region of the topsheet is formed of a fibrous nonwoven fabric in which most of fibers of the topsheet has a fiber orientation extending along one of the longitudinal direction and the transverse direction, and the region formed with the at least one indicator extends in one of the longitudinal direction and the transverse direction so that the direction in which the region formed with the indicators extends is coincident with the fiber orientation of the topsheet.

Advantageous Effects of Invention

Particularly according to one or more embodiments of the present invention, the liquid-absorbent structure is interposed between the top- and backsheets, and the hydrophilic bottom sheet is located between the bottom surface of the core of the liquid-absorbent structure and the wrapping sheet adapted to wrap the core. The backsheet is formed with the indicators so that the indicators may be directly put in contact with the wrapping sheet. The oil absorbency of the wrapping sheet is set to be higher than that of the bottom sheet and thereby it is possible to prevent the indicators from being transferred to the liquid-absorbent structure. Further, in response of discharge of body exudates, the indicators can be caused to develop the color reaction.

DESCRIPTION OF EMBODIMENTS

Figure 1:
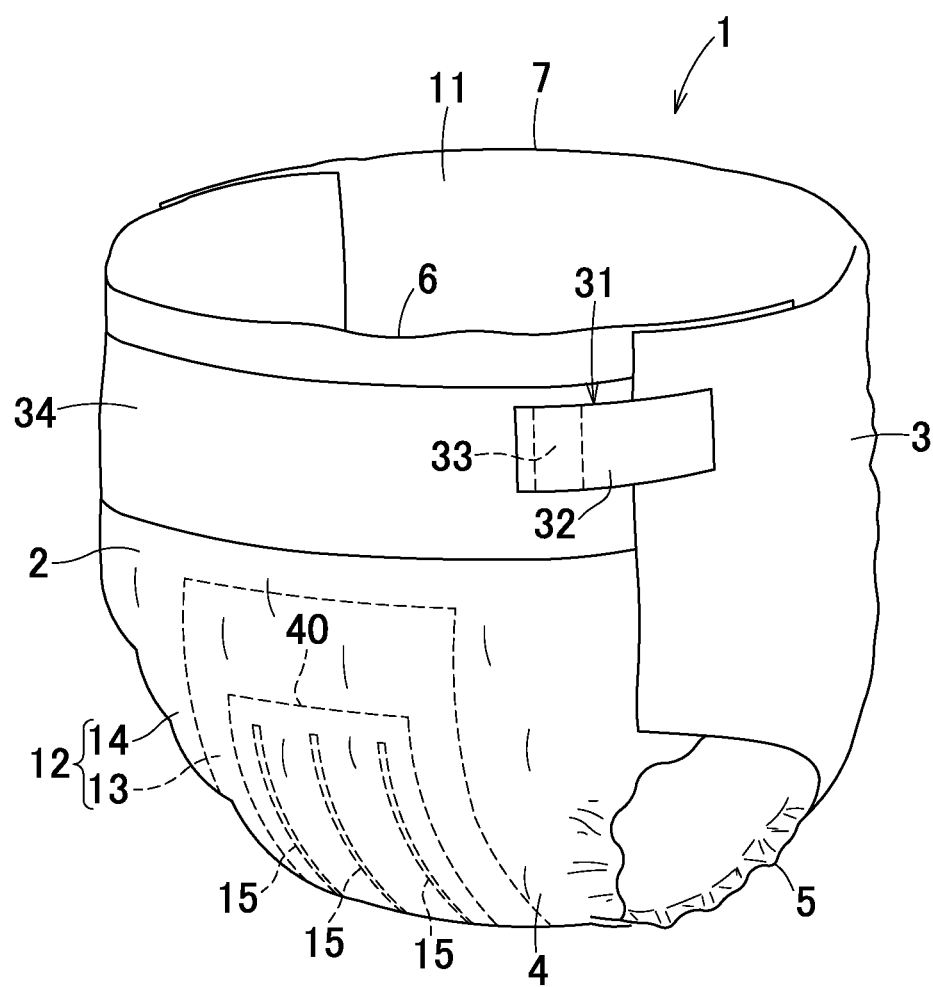
FIG. 1 is a perspective view of a disposable diaper as one embodiment of the disposable wearing article.
Figure 1:
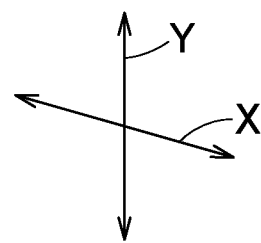
Figure 2:
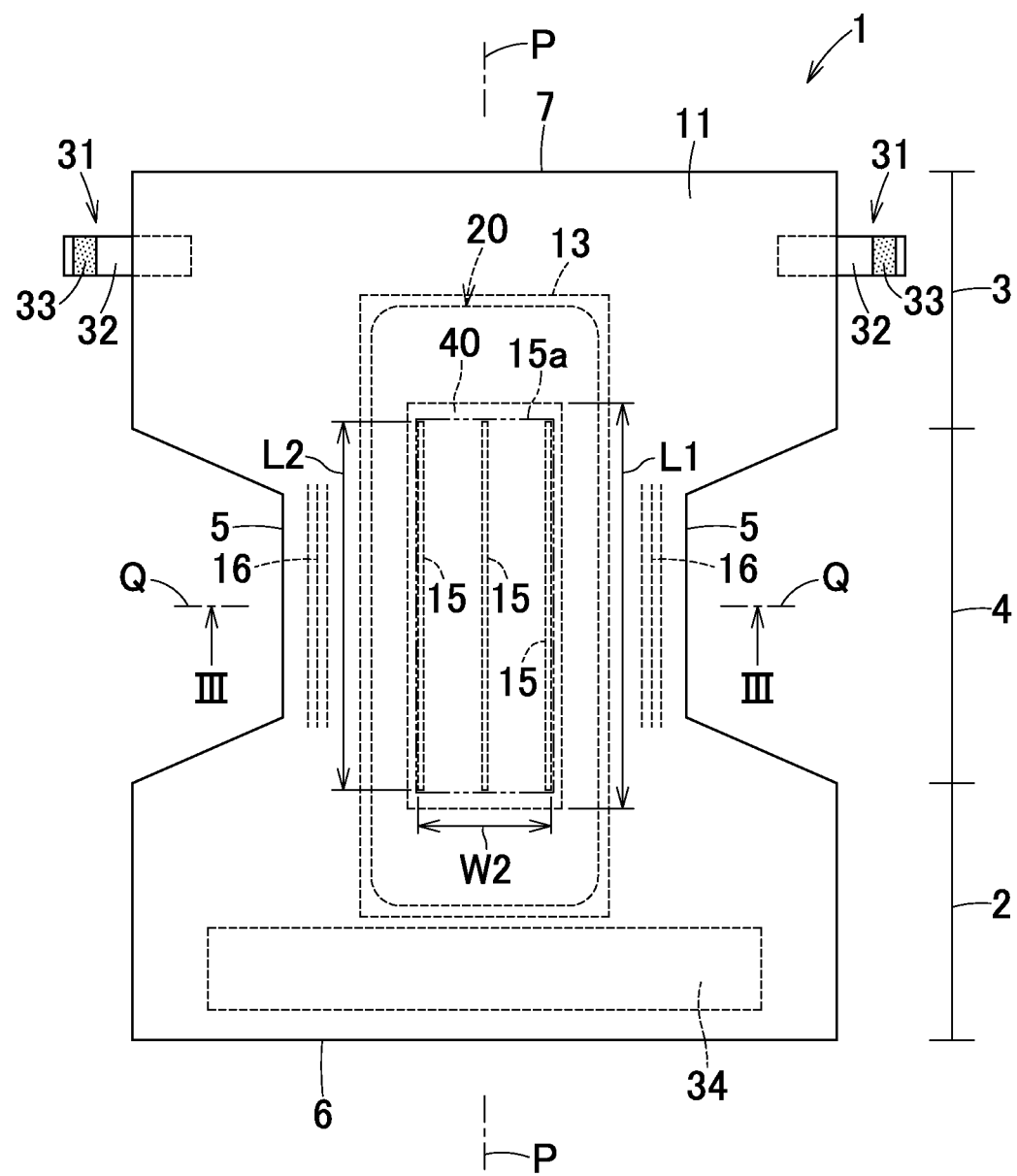
FIG. 2 is a developed plan view of the diaper.
Figure 3:
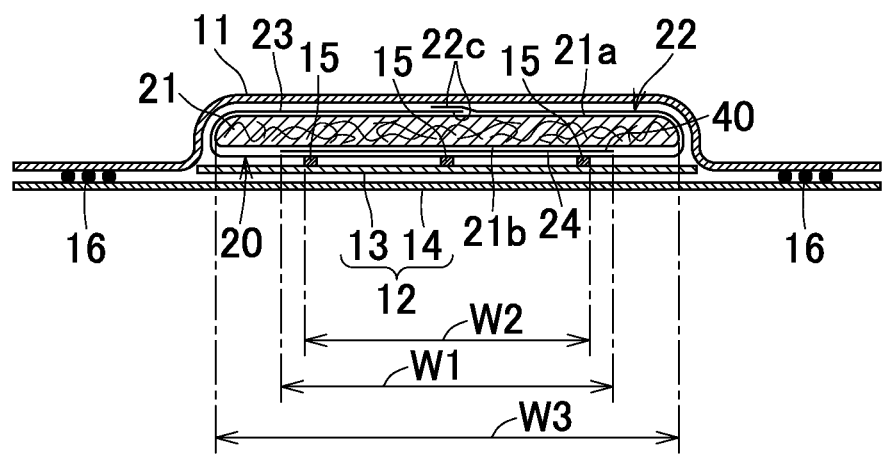
FIG. 3 is a sectional view taken along line III-III in FIG. 2.
Figure 4:
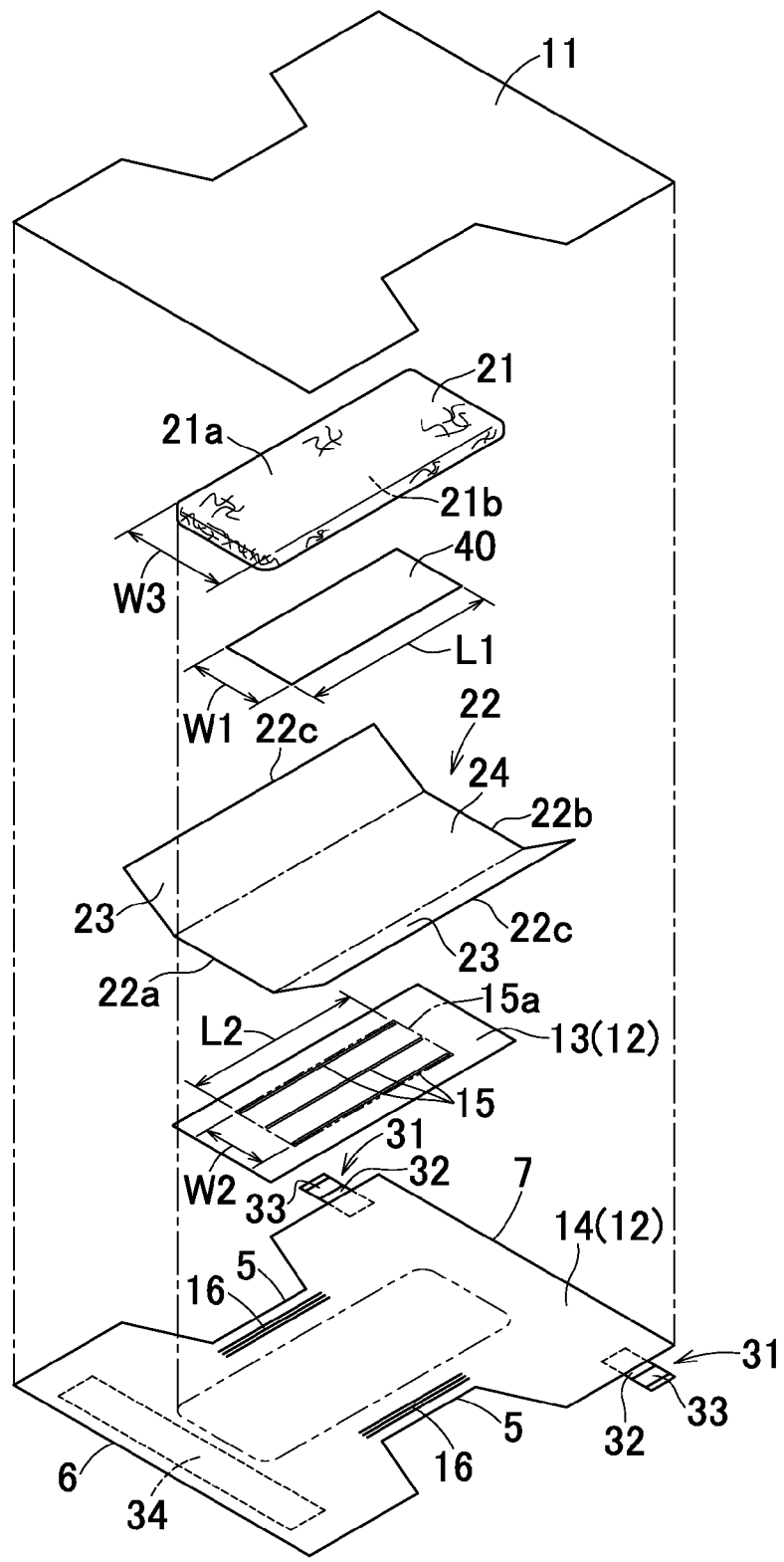
FIG. 4 is an exploded perspective view of the diaper.

FIG. 1 is a perspective view of a disposable diaper 1 illustrated as an example of a disposable wearing article according to the present invention, FIG. 2 is a developed plan view of the diaper 1 as viewed from the side of a wearer's body, FIG. 3 is a sectional view taken along line III-III in FIG. 2, and FIG. 4 is an exploded perspective view of the diaper 1. In FIGS. 2 through 4, respective elastics are illustrated in a state stretched against the contractile force. The diaper 1 has a longitudinal imaginary center line P-P bisecting a dimension of the diaper 1 in a transverse direction X and a transverse imaginary center line Q-Q bisecting a dimension of the diaper 1 in a longitudinal direction Y wherein the diaper 1 is symmetric about the longitudinal imaginary center line P-P.

The diaper 1 has a skin-facing side facing the wearer's body and a non-skin-facing side opposite to the skin-facing side (side facing the wearer's garment), a front waist region 2, a rear waist region 3 and a crotch region 4 extending between the front and rear waist regions 2, 3, lateral edges 5 and front and rear ends 6, 7 extending in the transverse direction X in the front and rear waist regions 2, 3, respectively. The diaper 1 includes a liquid-permeable topsheet 11 lying on the skin-facing side, a backsheet 12 lying on the non-skin-facing side and a liquid-absorbent structure 20 interposed between these top- and backsheets 11, 12.

As a material of the topsheet 11, a liquid-permeable fibrous nonwoven fabric may be used and, more specifically, an air-through fibrous nonwoven fabric having a mass per unit area in a range of about 15 to about 35 g/m² may be used. According to this embodiment, an air-through fibrous nonwoven fabric having amass per unit area of about 25 g/m² is used. As a material of the backsheet 12, a laminate sheet composed of first and second backsheets 13, 14 so that the outer surface of the first backsheet 13 may be covered with the second backsheet 14. The second backsheet 14 is coextensive with the topsheet 11 and the first backsheet 13 may be smaller than the second backsheet 14. As a material of the first backsheet 13, for example, a breathable and liquid-impermeable plastic film having a mass per unit area in a range of about 10 to about 25 g/m². According to this embodiment, the mass per unit area is about 18 g/m². As a material of the second backsheet 14, a spunbonded/meltblown/spunbonded (SMS) fibrous nonwoven fabric having a mass per unit area in a range of about 15 to about 35 g/m² may be used. According to this embodiment, this mass per unit area is about 17 g/m². By covering the first backsheet 13 with the second backsheet 14, a texture of the backsheet 12 can be improved.

The surface of the first backsheet 13 facing the liquid-absorbent structure 20 is formed with a plurality of indicators 15 adapted to develop a color reaction when coming in contact with at least one of moisture and body exudates. The plurality of indicators 15 extend in the longitudinal direction Y at intervals in the transverse direction X. In this regard, these indicators 15 may be provided at least in the crotch region 4 and across the crotch region 4 into the front and rear waist regions 2, 3. A region 15a formed with the indicators 15 in this manner extends in the longitudinal direction Y. The region 15a is measured off by a dimension W2 between the opposite outermost indicators 15 and a dimension L2 in the longitudinal direction Y of the respective indicators 15. As used herein, the phrase such region 15a extends in the longitudinal direction Y" means that the dimension L2 in the longitudinal direction Y is set to be larger than the dimension W2 in the transverse direction X.

The indicators 15 contain a hot-melt polymer, an indicator agent adapted to develop a color reaction and a plasticizing oil. As the polymer, the polymer commonly used for a hot melt adhesive such as polyethylene glycol may be used and, as the indicator agent, a pH-indicating agent such as bromocresol green, ethyl red, bromophenol blue or resazurin may be used. As the plasticizing oil, a paraffinic oil, a naphthenic oil, a compound derived from fatty acids, a compound derived from aromatic carboxylic acids or a mixture thereof may be used. In this regard, the indicators 15 containing a thickener resin or a wax diluting solvent may be also used.

A plurality of leg elastics 16 extending in the longitudinal direction Y is attached between the top- and backsheets 11, 12. These leg elastics 16 are attached under tension and in a contractible manner in the longitudinal direction Y along the lateral edges 5 of the diaper 1 between the top- and backsheets 11, 12 so as to extend across at least the crotch region 4. The leg elastics 16 are secured to at least one of the top- and backsheets 11, 12 by securing means such as a hot melt adhesive (not shown). Under the effect of these leg elastics 16 attached in such a manner, the lateral edges of the diaper 1 may be put in close contact with vicinities of the wearer's thighs, thereby preventing body exudates such as urine from leaking out from the gaps between the thighs and the diaper 1.

The non-skin-facing side of the backsheet 12 is formed with a pair of first fastening means 31. The first fastening means 31 are attached to the rear waist region 3 and each of the first fastening means 31 includes a tape tab 32 extending outwardly in the transverse direction X from the backsheet 12 and hook elements 33 attached to a distal portion. The non-skin-facing side of the backsheet 12 in the front waist region 2 is formed with a second fastening means 34 adapted to be releasably engaged with the first fastening means 31. The second fastening means 34 includes loop elements adapted to be releasably engaged with the hook elements 33 and extends in the transverse direction X between the lateral edges 5. The first fastening means 31 may put in engagement with the second fastening means 34 to configure the pants-type diaper 1 as shown in FIG. 1.

As exemplarily illustrated in FIGS. 3 and 4, the liquid-absorbent structure 20 includes a liquid-absorbent core 21 and a wrapping sheet 22 used to wrap the core 21. The core 21 has an absorbing surface 21a lying on the skin-facing side, i.e., the side of the topsheet 11 and a bottom surface 21b lying on the non-skin-facing side opposite to the absorbing surface 21a, i.e., on the side of the backsheet 12. As a material of the core 21, for example, fluff wood pulp and superabsorbent polymer particles may be used and, according to this embodiment, a mixture of fluff wood pulp and superabsorbent polymer particles is used. The content of superabsorbent polymer particles may be in a range of about 35 to about 70% by mass of a total mass of the core 21 and preferably in a range of about 45 to about 55% by mass.

The wrapping sheet 22 has front and rear ends 22a, 22b extending in the transverse direction X and lateral edges 22c extending in the longitudinal direction Y wherein the lateral edges 22c are folded onto each other on the absorbing surface 21a. The wrapping sheet 22 includes an absorbing region 23 adapted to wrap the absorbing surface 21a of the core 21 and a bottom surface region 24 adapted to wrap the bottom surface 21b. The absorbing region 23 and the bottom surface region 24 are formed of a single sheet folded outboard of the core 21 in the transverse direction X so as to be integrally continuous. As a material of the wrapping sheet 22, for example, tissue paper preferably having a mass per unit area in a range of about 10 to about 25 $g/m^2$.

Between the bottom surface 21b of the core 21 and the bottom surface region 24 of the wrapping sheet 22, a hydrophilic bottom sheet 40 is interposed. As a material of the bottom sheet 40, for example, a fibrous nonwoven fabric treated to become hydrophilic may be used. For example, a spunbonded/meltblown/spunbonded (SMS) fibrous nonwoven fabric having a mass per unit area in a range of about 10 to about 50 $g/m^2$ or a spunbonded fibrous nonwoven fabric having a mass per unit area in a range of about 15 to about 50 $g/m^2$ may be used.

A dimension W1 in the transverse direction X of the bottom sheet 40 is larger than the dimension W2 in the transverse direction X of the region 15a formed with the indicators 15 and smaller than a dimension W3 in the transverse direction X of the core 21. A dimension L1 in the longitudinal direction Y of the bottom sheet 40 is larger than the dimension L2 in the longitudinal direction Y of the indicators formed region 15a.

Most of component fibers of the wrapping sheet 22 and the bottom sheet 40 are oriented in the same direction in a carding step or any other step of forming these sheets 22, 40. According to the illustrated embodiment, these wrapping sheet 22 and the bottom sheet 40 are arranged so as for most of the component fibers to have the orientation along the longitudinal direction Y. A Klemm's water absorbency in the longitudinal direction Y of the wrapping sheet 22 is in a range of about 30 to about 45 mm, preferably in a range of about 33 to about 45 mm, and about 38 mm according to the illustrated embodiment. A Klemm's water absorbency in the transverse direction X is in a range of about 25 to about 40 mm, preferably in a range of about 30 to about 40 mm, and about 35 mm according to the illustrated embodiment. A Klemm's water absorbency in the longitudinal direction Y of the bottom sheet 40 is in a range of about 10 to about 35 mm, preferably in a range of about 12 to 30 mm and about 15 mm according to the illustrated embodiment. A Klemm's water absorbency in the transverse direction X is in a range of about 7 to about 25 mm, preferably in a range of about 10 to about 20 mm, and about 10 mm according the illustrated embodiment. The Klemm's water absorbency of the wrapping sheet 22 and the bottom sheet 40 is lower in the transverse direction X than in the longitudinal direction Y due to the fiber orientation of these sheets. The Klemm's water absorbency was measured in accordance with JIS-P8141.

The Klemm's water absorbency of the wrapping sheet 22 in at least one of the longitudinal direction Y and the transverse direction X is set to be higher than that of the bottom sheet 40 in the corresponding direction. In other words, the wrapping sheet 22 has a liquid diffusivity higher than that of the bottom sheet 40. In this way, urine discharged within the diaper 1 permeates the topsheet 11 and reaches the liquid-diffusive wrapping sheet 22, thereupon diffused from the absorbing region 23 toward the bottom surface region 24. The indicators 15 are arranged adjacent to the bottom surface region 24 and therefore urine diffused over the wrapping sheet 22 quickly causes the indicators 15 to develop a color reaction.

Assuming that a large amount of urine exceeding the liquid diffusivity of the wrapping sheet 22 is discharged, such urine permeates the wrapping sheet 22 and is absorbed by the absorbing surface 21a toward the bottom surface of the core 21. The bottom sheet 40 is arranged adjacent to the bottom surface 21b and therefore urine permeates this bottom sheet 40, then permeates the bottom surface region 24 of the wrapping sheet 22 and reaches the indicators 15. A dimension W1 in the transverse direction X of the bottom sheet 40 is smaller than the dimension W3 of the core 21 and outboard of the bottom sheet 40 in the transverse direction X, a surplus amount of urine moves directly to the bottom surface region 24 of the wrapping sheet 22 without permeating the bottom surface 40 and then reaches the indicators 15. In this manner, when a relatively large amount of urine is discharged, the indicators 15 may develop the color reaction by contacting urine having diffused over the wrapping sheet 22, urine having permeated the core 21 and the bottom sheet 40 and urine having permeated the core 21 outside the bottom sheet 40. In this regard, a certain amount of urine can be absorbed not only through the absorbing surface 21a but also through the bottom surface 21b of the core 21.

In the above-mentioned diaper 1, the liquid-diffusive wrapping sheet 22 is put in direct contact with the indicators 15 and whereby it is possible to make the indicators 15 to develop a color reaction already before any amount of urine permeates the bottom sheet 40. Even if an amount of urine is relatively small, urine can diffuse over the wrapping sheet 22 thereby making the indicators 15 develop a color reaction.

In the diaper 1 as has been described above, the core 21 contains the superabsorbent polymer particles having a particularly high water absorbability and there is a likelihood that these particles might absorb water vapor in the atmosphere. However, the hydrophobic bottom sheet 40 is disposed between the core 21 and the indicators 15 and this bottom sheet 40 can prevent the water vapor within the core 21 from permeating the bottom sheet 40, thereby preventing the indicators 15 from developing the color reaction due to such water vapor.

An oil absorbency of the wrapping sheet 22 in the longitudinal direction Y is in a range of about 10 to about 25 mm, preferably in a range of about 15 to about 25 mm, and about 17 mm in the illustrated embodiment. An oil absorbency of the wrapping sheet 22 in the transverse direction X is in a range of about 10 to about 25 mm, preferably in a range of about 15 to about 25 mm, and about 18 mm in the illustrated embodiment. An oil absorbency of the bottom sheet 40 in the longitudinal direction Y is in a range of about 6 to about 12 mm, preferably in a range of about 6 to about 9 mm, and about 8 mm in the illustrated embodiment. An oil absorbency of the bottom sheet 40 in the transverse direction X is in a range of about 6 to about 12 mm, preferably in a range of about 6 to about 9 mm and about 7 mm in the illustrated embodiment. In this regard, it is important that the absorbency of the wrapping sheet 22 in at least one of the longitudinal direction Y and the transverse direction X is higher than the absorbency of the bottom sheet 40. In other words, it is important that the highest value of the absorbencies of the wrapping sheet 22 and the bottom sheet 40 as measured in the longitudinal direction Y and the transverse direction X is of the wrapping sheet 22.

The oil absorbency was measured on the basis of Klemm's method for measurement of water absorbency prescribed by JIS-P8141. According to JIS-P8141, an immersion container should be filled with water and a lower end of a test piece should be immersed into the water and, when an oil absorbency is measured, the immersion container should be filled with a paraffin oil and a lower end should be immersed into the paraffin oil. In this measurement, a paraffin oil of which a viscosity is in a range of 40 to 85 mm$^2$/S at a temperature of 37.8° was used. The other measurement conditions were the same as those for measurement of Klemm's water absorbency.

The oil absorbency of the wrapping sheet is set to be higher than that of the bottom sheet 40 as has been mentioned above. The indicators 15 contain an oil but the oil absorbency of the wrapping sheet 22 may be set to be higher than that of the bottom sheet 40 to prevent the oil from being transferred to the core 21. While the indicators 15 contain the oil, the oil absorbency may be regulated as has been described above to prevent the oil from being transferred to the core 21. Specifically, the absorbency of the wrapping sheet 22 is relatively high and, in consequence, the oil contained in the indicators 15 is transferred to the bottom surface region 24 of the wrapping sheet 22 and the bottom surface region 24 is colored by the indicator agent contained in the oil. In contrast, the absorbency of the bottom sheet 40 is lower than that of the wrapping sheet 22 and, in consequence, transfer of the oil from the wrapping sheet 22 to the bottom sheet 40 is inhibited and retained by the wrapping sheet 22. In this way, it is possible to prevent the oil from being transferred to the core 21. Transfer of the oil to the core 21 is prevented in this manner and, in consequence, the indicator agent contained in the oil may be prevented from being put in contact with water vapor absorbed by the core 21 from the atmosphere and developing a color reaction.

TABLE 1 indicates a result of experiment wherein a sheet was placed between the indicators 15 and the core and it was observed whether the indicators were transferred to the core side or not. In this experiment, the indicator (a mass per unit area of about 30 g/m$^2$) was applied to the first backsheet according to the illustrated embodiment. The respective sheets (first to seventh sheets corresponding to Test Sheets in TABLE 1) were layered, a filter sheet was placed on the uppermost sheet and this assembly was left as it is under a pressure of about 40 g/m$^2$ at a temperature of 50° C. and a humidity of 0% for 24 hours. Thereafter, it was visually checked whether the indicators reached or not the filter paper. The respective sheets were numbered in order from the sheet placed adjacent to the indicators as the first layer, the second layer and the third layer. As the sheets for the respective layers, tissue paper used as the wrapping sheet in the illustrated embodiment or a liquid-permeable SMS fibrous nonwoven fabric used as the bottom sheet in the illustrated embodiment. A mass per unit area of the tissue paper used in this experiment was about 17 g/m$^2$ and a mass per unit area of the SMS fibrous nonwoven fabric was about 10 g/m$^2$.

TABLE 1

| Test Piece | First layer | Second layer | Third layer | Transfer to filter paper |
|---|---|---|---|---|
| 1 | Tissue paper | — | — | Observed |
| 2 | SMS fibrous nonwoven fabric | — | — | Observed |
| 3 | SMS fibrous nonwoven fabric | SMS fibrous nonwoven fabric | — | Observed |
| 4 | SMS fibrous nonwoven fabric | SMS fibrous nonwoven fabric | SMS fibrous nonwoven fabric | Observed |
| 5 | Tissue paper | SMS fibrous nonwoven fabric | — | Not observed |
| 6 | Tissue paper | SIMS fibrous nonwoven fabric | SMS fibrous nonwoven fabric | Not observed |
| 7 | Tissue paper | SMS fibrous nonwoven fabric | Tissue paper | Not observed |

Referring to TABLE 1, when only tissue paper or only an SMS fibrous nonwoven fabric was placed between the indicators and the core, the transfer of the indicators to the filter paper was observed (in Test Pieces Nos. 1 and 2). Also when two or three layers of tissue paper were placed between the indicators and the core, the transfer of the indicators to the filter paper (in Test Pieces Nos. 3 and 4) was observed. When an SMS fibrous nonwoven fabric was placed on tissue paper between the indicators and the core, the transfer of the indicators to the filter paper were not observed (in Test Piece No. 5) and an advantageous effect of the illustrated embodiment was verified. Also when tissue paper or an SMS fibrous nonwoven fabric was further placed as the third layer after an SMS fibrous nonwoven fabric was layered on tissue paper, the transfer of the indicator to the filter paper were not observed (Test Pieces Nos. 6 and 7). From such experimental result, it can be understood that it is important to place the wrapping sheet in contact with the indicators and to place the bottom sheet on the wrapping sheet in order to prevent the indicators from being transferred to the filter paper, and even when the other sheet is placed on the bottom sheet, such effect can be ensured.

The indicators 15 contain a hot-melt polymer and applied in a molten state to the first backsheet 13 and the liquid-absorbent structure 20 is layered thereon before the indicators get cool and solidified. While the indicators 15 in a molten state may be transferred to the bottom surface region 24 of the wrapping sheet 22 more easily than in its solidified state, the above-mentioned arrangement can reliably prevent the indicators from being transferred to the core 21. The indicators 15 transferred to the bottom surface region 24 can develop its color reaction. Before urine reaches the first backsheet 13 coated with the indicator 15, the indicators 15 already having been transferred to the bottom surface region 24 develops a color reaction and therefore the occurrence of urination can be detected further quickly.

The indicators 15 are arranged to extend in the longitudinal direction Y and to be spaced apart from each other in the transverse direction X. With such an arrangement, if urination is of a relatively small amount, such a small amount of urine may be transferred from the absorbing region 23 directly to the bottom surface region 24 and scarcely be absorbed by the core 21. In this case, only the outermost indicators 15 in the transverse direction X may develop a color reaction and the middle indicator 15 may develop no or little color reaction. Therefore, based on a degree of color reaction developed by the individual indicators 15, an amount of urination may be judged. While a plurality of the indicators 15 is formed in the illustrated embodiment, it is possible to arrange a single indicator 15 and/or to provide the indicator(s) not in the form of linear indicator(s) but in the form of graphic(s) or letter(s). Further, it is also possible to arrange the indicator(s) 15 to extend in the transverse direction X.

While the bottom surface region 24 and the backsheet 12 are joined to each other by joining means such as a hot melt adhesive (not shown), such a joining means is preferably applied at certain intervals so that the joining means should not interfere with a flow of urine.

In the illustrated embodiment, a content percentage of the superabsorbent polymer particles in the core 21 is in a range of about 35 to about 70% by mass and by setting the content percentage of the superabsorbent polymer particles to a relatively high level, it is possible to reduce a thickness dimension of the core 21 to about 1.0 to about 3.5 mm. With increase in a content of the superabsorbent polymer particles, the core 21 is more likely to absorb water vapor in the atmosphere. However, use of the bottom sheet 22 makes it possible to prevent the indicator 15 from developing a color reaction due to the water vapor absorbed by the core 21 in the diaper 1 before it is actually used. Usually, the superabsorbent polymer particles are mixed with fluff wood pulp fibers so that the superabsorbent polymer particles may be retained among the fluff wood pulp. However, when the content percentage of the superabsorbent polymer particles is relatively high, some of the superabsorbent polymer particles might drop out of the fluff pulp. Even when such dropped out superabsorbent polymer particles gather in the bottom surface region 24 and water vapor in the atmosphere is absorbed by them, the indicator 15 may be prevented from developing a color reaction due to such water vapor.

While the wrapping sheet 22 and the bottom sheet 40 are layered on each other so that the fiber orientations of these two sheets may be coincident with each other in the illustrated embodiment, these two sheets may be layered so that the fiber orientations of these two sheets may intersect with each other. According to the illustrated embodiment, the fiber orientations of most of fibers of these two sheets extend in the longitudinal direction Y and whereby the diffusion of urine in the longitudinal direction Y is improved. Considering that the liquid-absorbent structure 20 has a rectangular shape which is relatively long in the longitudinal direction Y, the fiber orientation thereof is selected to extend in the longitudinal direction Y so that body exudates can be absorbed by the core 21 over its range as large as possible. However, the fiber orientation of the wrapping sheet 22 and the bottom sheet 40 is not limited thereto. Particularly when the fiber orientation is selected to extend in the transverse direction X, the diffusion of urine can be accelerated in the transverse direction X and whereby a time required for urine to reach the indicators 15 can be further shortened. In this way, the indicators can quickly develop the color reaction in response to urination.

While the single bottom sheet 40 is provided between the wrapping sheet 22 and the core 21 according to the illustrated embodiment, it is possible to provide two or more bottom sheets 40 layered between the wrapping sheet 22 and the core 21. By layering a plurality of the bottom sheets 40 in this manner, the water vapor contained in the core 21 can be further reliably prevented from coming in contact with the indicators 15 and, at the same time, the oil of the indicators 15 can be prevented from being transferred back to the core 21.

While the absorbing region 23 and the bottom surface region 24 are defined by folding the single wrapping sheet 22 outboard of the core 21 in the transverse direction X according to the illustrated embodiment, a manner in which the absorbing region 23 and the bottom surface region 24 are defined is not limited to this manner. For example, it is possible to provide a first wrapping sheet adapted to wrap the absorbing surface 21a of the core 21 and a second wrapping sheet adapted to wrap the bottom surface 21 of the core 21 and these two wrapping sheets may be joined at least outboard of the core 21 in the transverse direction X, for example, with a hot melt adhesive, a heat sealing technique or an ultrasonic sealing technique.

Figure 5:
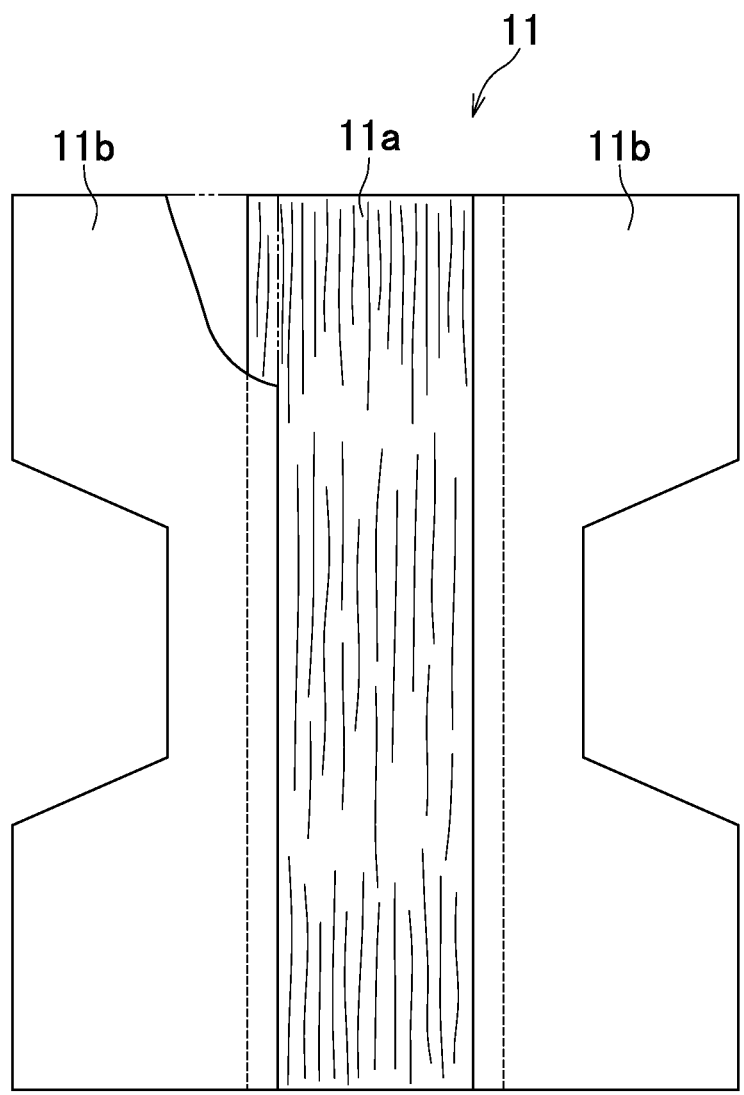
FIG. 5 is a plan view illustrating another example of a topsheet.
Figure 6:
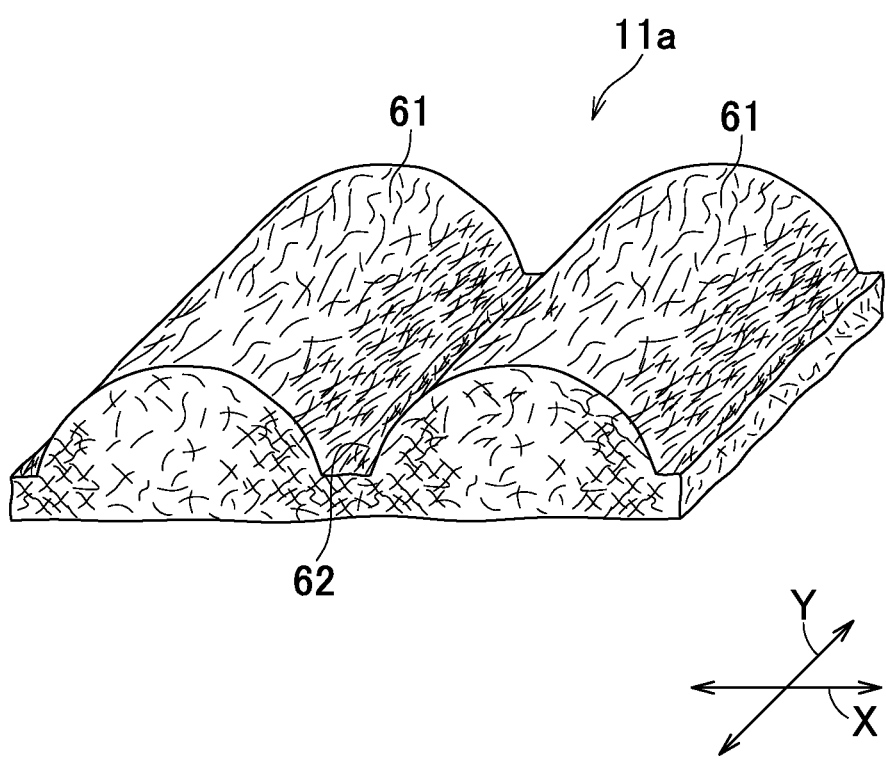
FIG. 6 is a scale-enlarged diagram illustrating part of FIG. 5.

FIGS. 5 and 6 illustrate still another example of this embodiment wherein FIG. 5 is a partially cutaway plan view of the topsheet 11 and FIG. 6 is an scale-enlarged perspective view illustrating part of a central sheet 11a defining a center region of the topsheet 11. According to this embodiment, the topsheet 11 includes a generally rectangular central sheet 11a in which most of fibers of the central sheet 11a has a fiber orientation in the longitudinal direction Y and opposite lateral sheets 11b lying outboard of the central sheet 11a in the transverse direction X. At least the central sheet 11a is formed of a liquid-permeable fibrous nonwoven fabric characterized by including a plurality of ridges 61 extending in the longitudinal direction Y and a plurality of grooves 62 defined between each pair of the adjacent ridges 61 and extending in the longitudinal direction Y. The lateral sheets 11b may be formed of a liquid-permeable or liquid-impermeable fibrous nonwoven fabric. The other arrangements are similar to those in the diaper 1 illustrated in FIGS. 1 through 4.

The central sheet 11a may be formed with the ridges 51 and the grooves 62, for example, by subjecting the regions of the central sheet 11a to be formed with the grooves to gaseous fluid jets, for example, hot air jets. By subjecting the sheet 11a to the above-mentioned fluid jets, most of the fibers in the respective grooves 62 are forcibly drifted toward both sides, substantially maintaining the fiber orientation in the respective grooves 62 in the longitudinal direction Y. In this way, the fibers oriented in the longitudinal direction Y are more than the fibers oriented in the transverse direction X in the central sheet 11a and, thus, as a whole, the fiber orientation in the longitudinal direction X can be conspicuous.

A dimension in the transverse direction X of the central sheet 11a is preferably equal to or larger than a dimension in the transverse direction X of the core 21. Measurement of the fiber orientation of the central sheet 11a may be carried out, for example, with use of Digital Microscope VHX-100 manufactured by Keyence Corporation. Specifically, within a certain definite range of the observed image data, the fiber falling within the range of +45° to −45° to imaginary lines extending in parallel in the longitudinal direction is determined to be oriented in the longitudinal direction and the fiber falling within the range of +45° to −45° to imaginary lines extending in parallel in the transverse direction is determined to be oriented in the transverse direction. A percentage of total number of fibers oriented in the longitudinal direction and a percentage of total number of fibers oriented in the transverse direction may be calculated to measure/calculate the fiber orientation. For example, if the number of fibers observed to be oriented in the longitudinal direction is 55% or more of the total number of fibers, i.e., 100%, it may be determined that the sheet has the fiber orientation along the longitudinal direction. In this regard, the method for determination of the fiber orientation is not limited to the above-mentioned measurement and it is also possible to determine the fiber orientation by measuring a tensile strength of the sheet. Specifically, a test piece extending in the longitudinal direction of the sheet and a test piece extending in the transverse direction may be prepared and a tensile strength under a predetermined tensile load may be measured with use of a tensile tester. If the tensile strength of the test piece extending in the longitudinal direction is higher than that of the test piece extending in the transverse direction, it may be determined that the sheet has the fiber orientation along the longitudinal direction.

The topsheet 11 is placed so that the fiber orientation of the central sheet 11a thereof may be coincident with the longitudinal direction Y and the indicators 15 formed region 15a is also placed so as to extend in the longitudinal direction Y. In other words, the fiber orientation of the central sheet 11a is coincident with the direction in which the indicators formed region 15a extends. Urine discharged onto the central sheet 11a is diffused in the longitudinal direction Y along the fiber orientation thereof. The urine diffused in this manner moves through the liquid-absorbent structure 20 to the indicators 15 and comes in contact with the region 15a over a further wide range thereof and makes the indicators 15 to develop the color reaction over a correspondingly wide range since the indicators formed region 15a extends in the longitudinal direction Y. The color reaction developed by the indicators 15 over a wide range in this manner makes it possible to improve a visibility of urination. Particularly in the diaper 1 having the dimension in the longitudinal direction Y larger than that in the transverse direction X, the fiber orientation of the central sheet 11a as well as the indicators 15 formed region 15a be selected to extend in the longitudinal direction Y to further improve the visibility of the indicators 15.

The constituent members of the diaper 1 are not limited to those described in this specification but the other types of material widely used in the relevant technical field may be used without limitation. The terms "first" and "second" used in this specification are used merely to distinguish the similar elements, similar positions or the other similar means. While the diaper 1 of open-type has been described, the present invention is applicable also to a pull-on type diaper.

REFERENCE SIGNS LIST 1 disposable diaper (disposable wearing article)
2 front waist region
3 rear waist region
4 crotch region
11 topsheet
12 backsheet
15 indicator
20 liquid-absorbent structure
21 core
21a absorbing surface
21b bottom surface
22 wrapping sheet
40 bottom sheet
X transverse direction
Y longitudinal direction

The invention claimed is:

1. A disposable wearing article having a longitudinal direction and a transverse direction, including:
    a skin-facing side;
    a non-skin-facing side opposite to the skin-facing side;
    front and rear waist regions;
    a crotch region extending between the front and rear waist regions;
    a liquid-permeable topsheet lying on the skin-facing side
    a liquid-impermeable backsheet lying on the non-skin-facing side and;
    a liquid-absorbent structure interposed between these top- and backsheets and placed at least in the crotch region, wherein
    the backsheet is formed on the surface thereof facing the liquid-absorbent structure with at least one indicator adapted to develop a color reaction when the at least one indicator comes in contact with at least one of moisture and body exudates, wherein:
    the liquid-absorbent structure includes a liquid-absorbent core and a liquid-diffusive wrapping sheet adapted to wrap the skin-facing surface and the non-skin-facing surface of the core and being continuous outboard of the core in the transverse direction; and
    a bottom sheet formed of a hydrophilic fibrous nonwoven fabric is provided between the non-skin-facing surface of the core and the wrapping sheet so that the bottom sheet positionally corresponds to the at least one indicators wherein a dimension in the transverse direction of the bottom sheet is smaller than that of the core, so as to allow a surplus of urine discharged on the core to flow around the bottom sheet and the at least one indicator contains a hot-melt polymer, an indicator agent adapted to develop a color reaction and a plasticizing oil, and the at least one indicator is adapted to put in direct contact with the wrapping sheet, wherein an oil absorbency of the wrapping sheet is higher than that of the bottom sheet.

2. The disposable wearing article according to claim 1, wherein a Klemm's water absorbency of the wrapping sheet is higher than that of the bottom sheet.

3. The disposable wearing article according to claim 1, wherein most of fibers of the bottom sheet has a fiber orientation along one of the longitudinal direction and the transverse direction and a region formed with the at least one indicator extends along the fiber orientation of the bottom sheet.

4. The disposable wearing article according to claim 3, wherein most of fibers of the wrapping sheet have a fiber orientation extending in one of the longitudinal direction and the transverse direction, and the wrapping sheet and the bottom sheet are layered on each other so that the fiber orientations of these two sheets coincide with each other.

5. The disposable wearing article according to claim 1, wherein the core contains at least superabsorbent polymer particles and a content percentage of the superabsorbent polymer particles is in a range of 35 to 70% by mass of a total mass of the core.

6. The disposable wearing article according to claim 1, wherein a center region of the topsheet is formed of a fibrous nonwoven fabric in which most of fibers of the topsheet has a fiber orientation extending along one of the longitudinal direction and the transverse direction, and the region formed with the at least one indicator extends in one of the longitudinal direction and the transverse direction so that the direction in which the region formed with the indicators extends is coincident with the fiber orientation of the topsheet.

* * * * *